US010182840B2

(12) United States Patent
Raybin et al.

(10) Patent No.: US 10,182,840 B2
(45) Date of Patent: Jan. 22, 2019

(54) TISSUE RESECTION DEVICE AND RELATED METHODS OF USE

(71) Applicant: Boston Scientific Scimed, Inc., Maple Grove, MN (US)

(72) Inventors: Samuel Raybin, Marlborough, MA (US); Paul Smith, Smithfield, RI (US); Brian Gaffney, Rutland, MA (US); Naroun Suon, Lawrence, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1125 days.

(21) Appl. No.: 14/509,801

(22) Filed: Oct. 8, 2014

(65) Prior Publication Data
US 2015/0105789 A1 Apr. 16, 2015

Related U.S. Application Data

(60) Provisional application No. 61/889,198, filed on Oct. 10, 2013.

(51) Int. Cl.
*A61B 17/3205* (2006.01)
*A61B 17/00* (2006.01)
(Continued)

(52) U.S. Cl.
CPC .................. *A61B 17/32056* (2013.01); *A61B 2017/00269* (2013.01); *A61B 2017/00526* (2013.01);
(Continued)

(58) Field of Classification Search
CPC ............ A61B 17/221; A61B 17/32056; A61B 2018/141; A61B 2018/1407; A61B 2017/320064
See application file for complete search history.

(56) References Cited

U.S. PATENT DOCUMENTS 8,157,811 B2 * 4/2012 Shinozuka ........... A61B 17/221
606/113
9,101,383 B1 * 8/2015 Dostal ............... A61B 17/32056
(Continued)

FOREIGN PATENT DOCUMENTS

EP 0 684 791 B1 3/2000
JP 2002095678 * 4/2002
(Continued)

OTHER PUBLICATIONS

International Search Report and Written Opinion for corresponding International Application No. PCT/US2014/059733 dated Nov. 26, 2014, (10 pages).

*Primary Examiner* — Matthew F Desanto
(74) *Attorney, Agent, or Firm* — Bookoff McAndrews, PLLC

(57) ABSTRACT

In accordance with an aspect of the present disclosure, the medical device includes a snare member having a proximal portion and a distal portion. The medical device also includes an operating member extending proximally of the snare member. The operating is enabled to extend and retract the snare member from a sheath. The snare member includes a transition portion extending between the proximal portion and the distal portion. The transition portion connects the proximal portion to the distal portion. The distal portion has a different cross-sectional area than the proximal section of the snare member.

20 Claims, 3 Drawing Sheets

(51) Int. Cl.
*A61B 17/32* (2006.01)
*A61B 18/14* (2006.01)

(52) U.S. Cl.
CPC ............ *A61B 2017/320064* (2013.01); *A61B 2018/141* (2013.01); *A61B 2018/1407* (2013.01); *Y10T 29/49* (2015.01)

(56) References Cited

U.S. PATENT DOCUMENTS

| | | | |
|---|---|---|---|
| 2011/0106077 A1* | 5/2011 | Yanuma | A61B 17/32056 606/45 |
| 2013/0018384 A1* | 1/2013 | Kappel | A61B 17/32056 606/111 |
| 2013/0184738 A1 | 7/2013 | Laroya et al. | |
| 2013/0211403 A1 | 8/2013 | Suon et al. | |

FOREIGN PATENT DOCUMENTS

| | | |
|---|---|---|
| JP | 2005/124696 | 5/2005 |
| WO | WO 2007/000452 A2 | 1/2007 |
| WO | WO 2013/101900 A1 | 7/2013 |

* cited by examiner

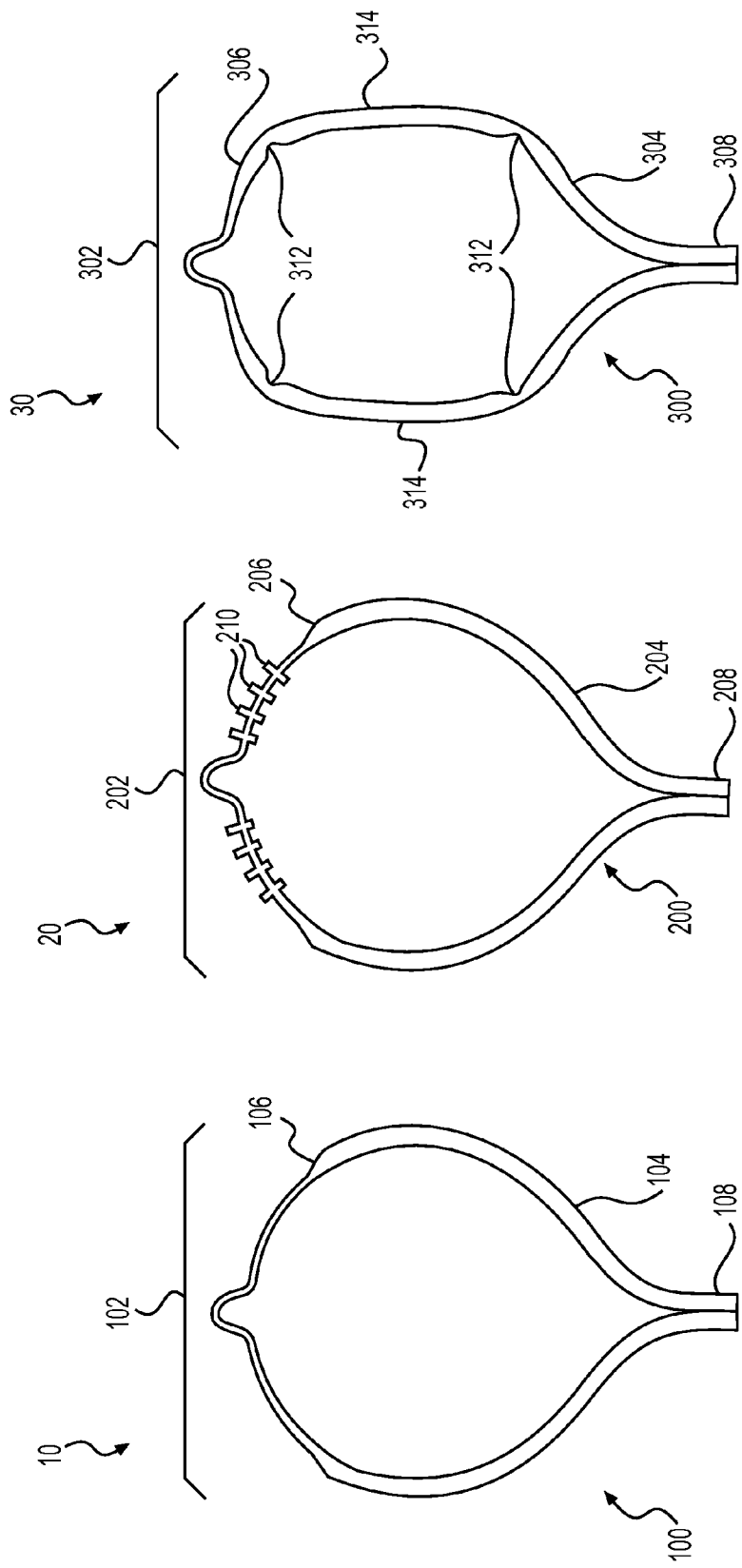

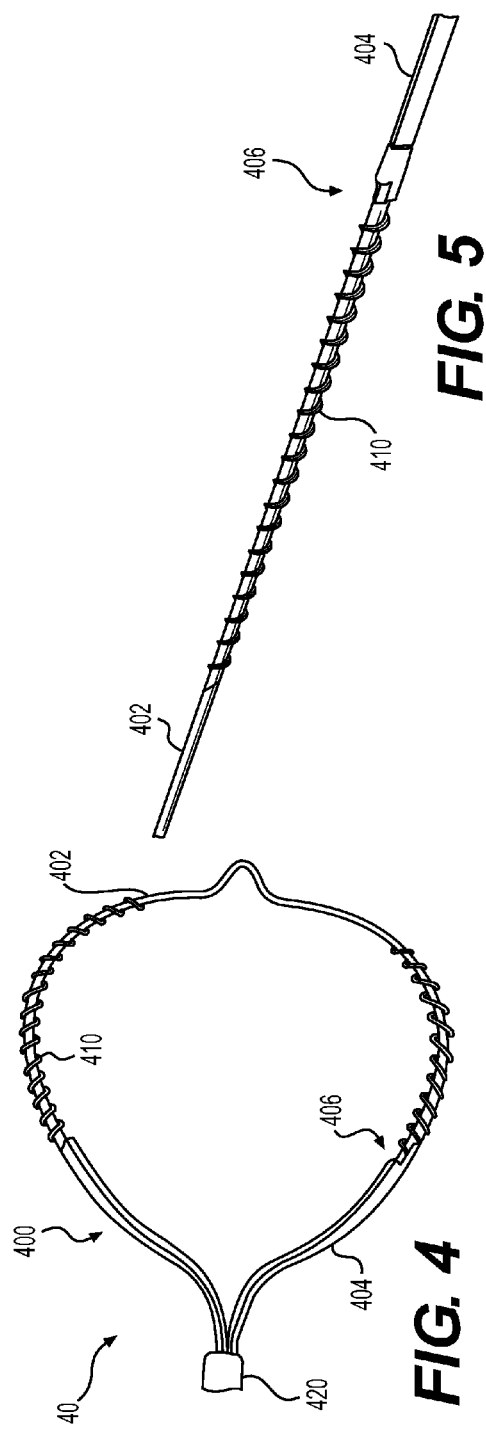
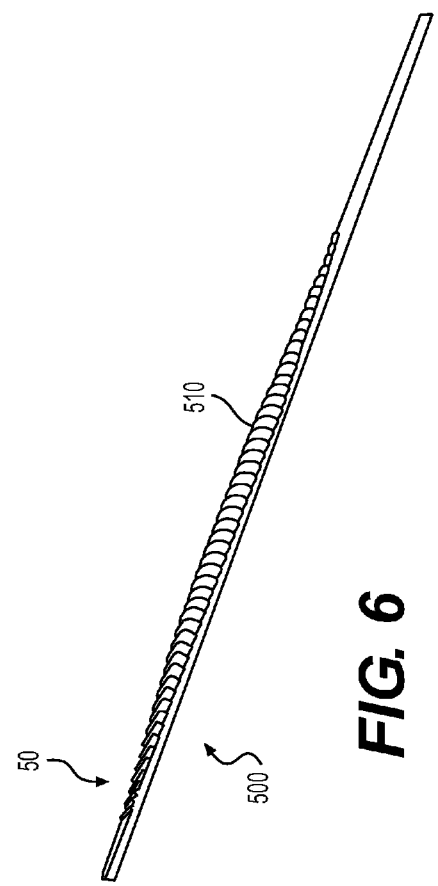
FIG. 4
FIG. 5
FIG. 6

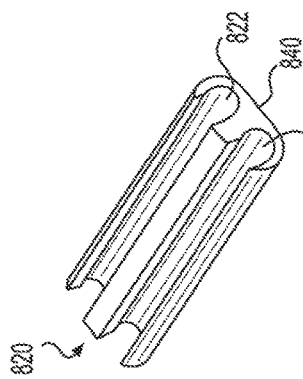
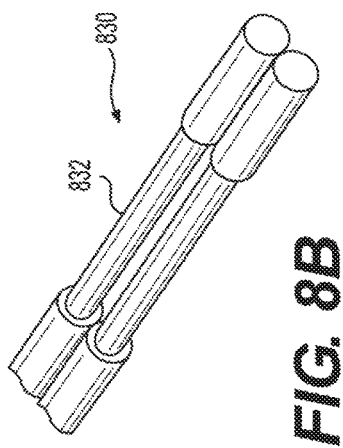
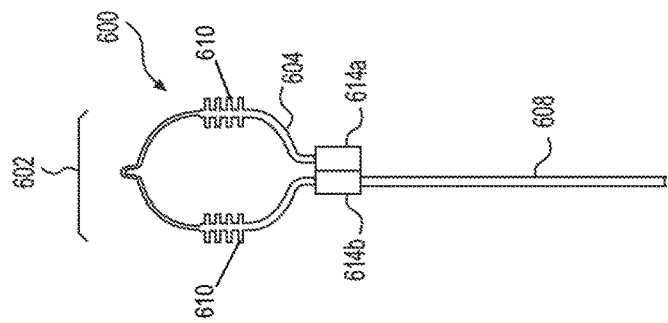
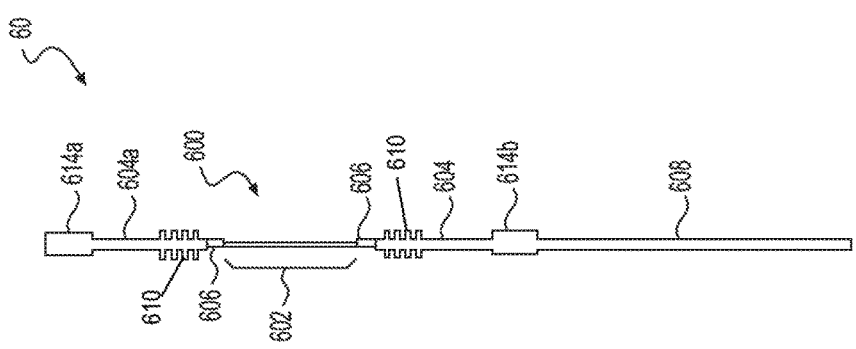

… … …

TISSUE RESECTION DEVICE AND RELATED METHODS OF USE

CROSS-REFERENCE TO RELATED APPLICATIONS

This application claims the benefit of U.S. Provisional Application No. 61/889,198, filed Oct. 10, 2013, the disclosure of which is incorporated herein by reference in its entirety.

SUMMARY

FIELD

Embodiments of the present disclosure relate generally to medical devices and procedures. In particular, embodiments of the present disclosure relate to medical devices and methods for tissue resection within the body of a patient.

BACKGROUND

A wide variety of medical techniques and instruments have been developed for diagnosis as well as treatment within the body of a patient, such as in the gastrointestinal (GI) tract. Medical procedures, including Endoscopic Mucosal Resection (EMR), Endoscopic Sub-mucosal Resection (ESR), Polypectomy, Mucosectomy, etc., are minimally invasive methods for severing and retrieving malignant and non-malignant lesions, e.g., polyps. Procedures such as, EMR involve resection of a lesion or unwanted tissue from a tissue wall within a body lumen. Snares have been commonly used during such medical procedures for resecting tissue from a target site. During resection procedures, physicians ensnare or capture a target tissue within a loop of the snare. Often, a physician may apply a downward force on the snare in an effort to improve snare traction around the target tissue and resect the target tissue closer to its base on the tissue wall. However, when such a downward force is applied, a distal portion of conventional snares have a tendency to deflect away from the tissue wall. Such snares may be stiff and may have insufficient traction on the tissue, and often require repeated efforts to resect the tissue before the procedure can be successfully completed. Stiffness may lead to deflection of the snare from the tissue wall, (e.g., deflection away from a tissue plane defined by the tissue wall). Also, deflection of the snare before resection can lead to an "angled cut" instead of an "even cut" (e.g., a cut substantially parallel to or coplanar with the tissue plane). As such, conventional snares conform poorly to the tissue plane during resection.

Furthermore, conventional snares often include a snare loop of uniform cross-section. As noted above, such snares tend to be stiff and deflect away from the tissue plane during resection. Additionally, the performance of such snares may suffer. For example, in embodiments employing electrosurgical energy, a uniform cross-section snare loop may include a greater surface area than a snare with a varied cross-section. A greater surface area may result in reduced current density delivered to the target tissue during cutting. Additionally, conventional thick (e.g., uniform cross-section) snare loops, due to their inherent stiffness, often require greater force to extend and retract the snare loop during a procedure, thereby reducing the smoothness and/or responsiveness of actuation by a physician. This, likewise, limits the geometry of the loop itself, since a round, open snare loop requires greater deformation in order to be drawn into a snare sheath, and stiff, opposing sides of the snare loop tend to twist away from the tissue plane during extension and refraction. Indeed, an excessively stiff snare loop can also increase risk of unintended tissue trauma and perforation.

A tool or device with increased flexibility and control for better functional performance and improved traction may provide consistent capture, excision, and/or removal of unwanted tissue without unintentionally damaging healthy surrounding tissue.

The exemplary features of the present disclosure are directed to improvements in tissue resection devices and methods.

Embodiments of the present disclosure relate to medical devices and methods for performing tissue resection.

In accordance with an aspect of the present disclosure, the medical device may include a snare member having a proximal portion and a distal portion. The medical device may also include an operating member extending proximally of the snare member. The operating member may be enabled to extend and retract the snare member. Further, the snare member may include a transition portion extending between the proximal portion and the distal portion. The transition portion may connect the proximal portion to the distal portion, wherein the distal portion may have a different cross-sectional area than the proximal section of the snare member.

The medical device may further include one or more of the following features: the cross-sectional area of the distal portion may be smaller than the cross-sectional area of the proximal portion and the cross-sectional shape of the distal portion may be circular and the cross-sectional shape of the proximal portion may be non-circular; at least one traction member that may extend along a first portion of the snare member, wherein the at least one fraction member may be a continuous spiral coiled around the first portion of the snare member; the at least one traction member may be a first traction member and the medical device may further include a second traction member extending along a second portion of the snare member opposite the first portion of the snare member, the second traction member may be a continuous spiral coiled around the second portion of the snare member; a plurality of traction members may be formed of a continuous piece of material with the snare member, wherein each of the plurality of traction members may be spaced from an adjacent traction member of the plurality of tractions members and may be configured to extend radially outwardly from the snare member; each of the plurality of traction members may have a cross-sectional shape selected from the following: rectangular, semi-circular, ovular, and polygonal, and wherein a first series of traction members is disposed on a first portion of the snare member and a second series of traction members is disposed on a second portion of the snare member opposite the first portion of the snare member; at least one of the plurality of traction members may have a different cross-sectional shape than at least one other of the plurality of traction members; and each of the plurality of the traction members may extend in the same direction outward from the snare member.

In accordance with another aspect of the present disclosure, a medical device may include a snare member having a proximal portion and a distal portion. The medical device may also include an operating member extending proximally of the snare member. The operating member may be configured to extend and retract the snare member. The snare member may include a transition portion extending between the proximal portion and the distal portion, connecting the proximal portion to the distal portion. The distal portion may be more flexible than the proximal section of the snare member.

The medical device may further include one or more of the following features: a cross-sectional area of the distal portion may be smaller than a cross-sectional area of the proximal portion, and a cross-sectional shape of the distal portion may be circular and a cross-sectional shape of the proximal portion may be non-circular; at least one traction member may extend along a first portion of the snare member, wherein the at least one fraction member may be a continuous spiral coiled around the first portion of the snare member; the at least one traction member may be a first traction member, the medical device may further include a second traction member which may extend along a second portion of the snare member opposite the first portion of the snare member, the second traction member may be a continuous spiral coiled around the second portion of the snare member; a plurality of traction members may be formed of a continuous piece of material with the snare member, each of the plurality of traction members may be spaced from an adjacent traction member of the plurality of traction members and may be configured to extend radially outwardly from the snare member; each of the plurality of the fraction members may have a cross-sectional shape selected from the following: rectangular, square, semi-circular, ovular, and polygonal, and a first series of traction members may be disposed on a first portion of the snare member and a second series of fraction members may be disposed on a second portion of the snare member opposite the first portion of the snare member; and at least one of the plurality of traction members may have a different cross-sectional shape than at least one other of the plurality of traction members.

In accordance with another aspect of the present disclosure, a method of forming a medical device may include forming a loop of a snare member. The snare member may have a proximal portion and a distal portion. The method may further include modifying the snare member to form a transition portion extending between the proximal portion and the distal portion. The transitional portion may connect the proximal portion to the distal portion. Modifying the snare member may include altering a cross-sectional area of the distal portion so as to be different than the cross-sectional area of the proximal portion.

The method may further include one or more of the following features: the cross-sectional area of the distal portion may be smaller than the cross sectional area of the proximal portion, and a cross-sectional shape of the distal portion may be circular and a cross-sectional shape of the proximal portion may be non-circular; forming at least first and second traction members, the first fraction member may extend along a first portion of the snare member, wherein the first traction member may be a continuous spiral coiled about the first portion of the snare member, the second traction member may extend along a second portion of the snare member opposite the first portion of the snare member, and the second traction member may be a continuous spiral coiled about the second portion of the snare member; forming a plurality of traction members which may be of a continuous piece of material with the snare member, each of the plurality of traction members may be spaced from an adjacent fraction member of the plurality of traction members and may be configured to extend radially outwardly from the snare member; and each of the plurality of the fraction members may have a cross-sectional shape selected from the following: rectangular, square, semi-circular, ovular, and polygonal, and a first series of traction members may be disposed on a first portion of the snare member and a second series of traction members may be disposed on a second portion of the snare member opposite the first portion of the snare member.

Additional objects and advantages of the present disclosure will be set forth in part in the description which follows, and in part will be understood from the description, or may be learned by practice of the claimed features. The objects and advantages of the claimed features will be realized and attained by means of the elements and combinations particularly pointed out in the appended claims.

It is to be understood that both the foregoing general description and the following detailed description are exemplary and explanatory only and are not restrictive of the disclosure, as claimed

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

FIG. 1 illustrates an exemplary resection device, according to an embodiment of the present disclosure;

FIG. 2 illustrates an exemplary resection device having one or more traction members, according to an embodiment of the present disclosure;

FIG. 3 illustrates an exemplary embodiment of a resection device including one or more stress relief portions, according to an embodiment of the present disclosure;

FIG. 4 illustrates an exemplary embodiment of a resection device, according to an embodiment of the present disclosure;

FIG. 5 illustrates an enlarged portion of the resection device of FIG. 4;

FIG. 6 illustrates an exemplary embodiment of a portion of a resection device depicting an arrangement of fraction members, according to an embodiment of the present disclosure;

FIG. 7A illustrates an exemplary embodiment of a resection device during manufacturing, according to an embodiment of the present disclosure;

FIG. 7B illustrates an exemplary embodiment of a resection device upon completion of manufacturing, according to an embodiment of the present disclosure;

FIG. 8A illustrates an exemplary embodiment of a coupler according to an embodiment of the present disclosure; and FIG. 8B illustrates an exemplary embodiment of a resection device configured for use with the coupler of FIG. 8A.

DETAILED DESCRIPTION

Reference will now be made in detail to embodiments of the present disclosure, examples of which are illustrated in the accompanying drawings. Wherever possible, the same reference numbers will be used throughout the drawings to refer to the same or like parts. The term "distal" refers to the direction that is away from the user and into the patient's body. By contrast, the term "proximal" refers to the direction that is closer to the user and away from the patient's body.

Overview

Embodiments of the present disclosure relate to medical devices and methods of manufacture and use for resecting and/or retrieving unwanted tissue such as cancerous tissues or lesions within a patient's body. For example, tissue disposed on the mucosal walls of the colon, esophagus, stomach, or duodenum may be targeted. A physician may desire to resect the tissue in order to conduct a biopsy or other examination. It should be noted that medical devices presented in the present disclosure can be used both for resecting and for retrieving target tissue or objects. However, for convenience, the term "resection device" will be used throughout this application.

In some embodiments, a resection device may include a snare member, and an operating member. The resection device may be used in conjunction with an elongate sheath e.g., an endoscope, a snare sheath or the like. The elongate sheath may include a lumen extending from a proximal end to a distal end of the elongate sheath. The distal end of the elongate sheath may include a distal opening at which the lumen may terminate. The snare member may be configured to transition between a first collapsed configuration within the lumen of the elongate sheath, and a second expanded configuration in which the snare member is caused to extend outwards from the distal opening of the elongate sheath. The operating member may be configured to extend and retract the snare member such that the snare member may transition between the expanded and the collapsed configurations. The operating member may include an actuating mechanism such as a push-pull member extending proximally of the snare member. Exemplary push-pull members will be discussed in detail with reference to subsequent figures.

Embodiments

FIG. 1 illustrates an exemplary resection device 10, according to an embodiment of the present disclosure. The resection device 10 may include a snare member 100 and an operating member, which may be a push-pull member 108. The snare member 100 may include a distal portion 102, a proximal portion 104, and one or more transition portions 106 extending between the proximal portion 104 and the distal portion 102.

The distal portion 102 and the proximal portion 104 of the snare member 100 may have different cross-sectional areas. For example, the distal portion 102 of the snare member 100 may have a smaller cross-sectional area than that of the proximal portion 104. The distal portion 102, due to its smaller cross-sectional area may exhibit increased flexibility. In particular, the increased flexibility of the distal portion 102 may allow improved conformance of the snare member 100 to the tissue plane during a resection procedure. That is, since the distal portion 102 is more flexible than the proximal portion 104, the distal portion 102 may bend and remain in contact with the tissue wall during a resection procedure. Said differently, the improved conformance of the snare member 100 with the tissue plane may allow distal portion 102 of the snare member 100 to deform and stay in contact with a tissue plane so as to capture the target tissue.

Variations in the cross-sectional area of the snare member 100 may be achieved by removing at least a portion of the material of the distal portion 102 through cutting, grinding, drawing, etching, machining, turning, stretching, hammering, and/or the like. In some embodiments, variations in cross-sectional area of the snare member 100 may be achieved by forming the distal portion 102 and the proximal portion 104 with materials having different material properties. For example, material variation could be achieved in a geometrically uniform or non-uniform cross-section snare member 100 by applying a heat-treating process to a portion (e.g., either the distal portion 102 or the proximal portion 104) of the snare member 100, or the snare member 100 may be constructed of varying materials that are welded and/or fused together. A combination of geometrical and material cross-sectional variations may be used for a more pronounced differentiation. For example, the snare loop 100 may be constructed of a first core material and a second coating material disposed about and co-extruded with the core material. The second coating material may be removed by any appropriate technique, such as, for example, grinding, turning, etching, etc., to form a reduced cross-sectional area distal portion 102 of snare member 100.

In some embodiments, variations in cross-section of the distal portion 102 and the proximal portion 104 may be achieved by varying cross-sectional shapes of the distal portion 102 and the proximal portion 104. For example, the distal portion 102 may have a circular or elliptical cross-sectional shape while the proximal portion 104 may have a rectangular or superelliptical cross-sectional shape. The cross-section of the distal portion 102 may allow it to be flexible and engage the tissue. However, the cross-section of the proximal portion 104 may provide suitable stiffness to enhance controllability and traction of the snare member 100.

As noted above, one or more transition portions 106 may extend between the proximal portion 104 and the distal portion 102. For example, two transition portions 106, positioned at opposing sides of snare member 100, may be employed as shown in FIG. 1. Transition portions 106 may be configured to bridge the proximal portion 104 to the distal portion 102 of snare member 100. Transition portions 106 include a variable geometrical cross-section. The variable geometrical cross-section of transition portions 106 may include a cross-sectional change which may be abrupt, sharp, or sudden. However, in some embodiments, the change in the cross-sectional area of the transition portions 106 may be a gradual taper. In such cases, the tapering may be linear (e.g., flat) or concave (e.g., rounded, arcuate) so as to include a radius of curvature.

The snare member 100 may be a wire in the form of a loop configured for surrounding and thereby severing and/or retrieving undesirable tissue. In some embodiments, the snare member 100 can be a monofilament wire or a multi-filament wire. The multifilament wire may be bonded, twisted together, crimped, and/or braided. In the illustrated embodiment, the snare member 100 may form a substantially circular loop shape. However, in some embodiments, the snare member 100 may be configured to have any suitable loop shape such as, but not limited to, oval, hexagonal, rectangle, square, irregular, polygonal, semicircular, octagonal or the like. Further, the snare member 100 can be formed using any suitable biocompatible material such as, but not limited to metals, polymers, alloys, or the like. Exemplary materials include steel, tungsten, NITINOL, or titanium, and so forth.

In some embodiments, the snare member 100 may be configured for electro-cauterization procedures. The snare member 100 and the push-pull member 108 may be formed from suitable conducting material, e.g., stainless steel, or NITINOL. The snare member 100 may be configured to transmit electric current within specific ranges and be able to withstand repeated heating cycles during electro-cauterization procedure. In some instances, the electric current passing through the reduced cross-sectional area of the distal portion 102 may be of higher density than the electric current passing through the proximal portion 104 having a larger cross-sectional area. Increased current density in the distal portion 102 may enable improved cutting of target tissue along the distal portion 102.

The push-pull member 108 (also referred to as legs) of the snare member 100 may connect the snare member 100 to a handle (not shown) located on a proximal end (not shown)

of the resection device outside the patient's body. The push-pull member 108 may be operable to extend and retract the snare member 100 and thereby transition the snare member 100 between the collapsed configuration and expanded configuration. For example, when a user applies an axial force in a distal direction through the handle, the push-pull member 108 may extend (e.g., push) the snare member 100 outwards from the elongate sheath (e.g., sheath 420 shown in FIG. 4), thus moving the snare member 100 into the expanded configuration. Similarly, when a user applies an axial force in a proximal direction through the handle, the push-pull member may retract (e.g., pull) the snare member 100 into the elongate sheath, thus moving the snare member 100 into the collapsed configuration. In some embodiments, the push-pull member 108 and the snare member 100 may be made of a continuous, e.g., monolithically formed unitary structure. However, in other embodiments, the push-pull member 108 and the snare member 100 may be discrete and coupled to one another using any suitable technique known in art. Exemplary techniques may include, welding, soldering, or heat bonding.

FIG. 2 illustrates an exemplary resection device 20 including a plurality of traction members 210, according to an embodiment of the present disclosure. While the embodiment of FIG. 2 illustrates a plurality of traction members 210, it is understood that in some embodiments, a single traction member 210 may be incorporated. The snare member 200 may include a distal portion 202 and a proximal portion 204. The distal portion 202 may have a cross-sectional area smaller than that of the proximal portion 204 as discussed above. Additionally, similarly to the embodiment of FIG. 1, snare member 200 may include transition portions 206 extending between the distal portion 202 and the proximal portion 204 of the snare member 200. Also, the snare member 200 may be coupled to push-pull member 208. The push-pull member 208 may be operable to extend and retract the snare member 200 and thereby transition the snare member 200 between the collapsed configuration and expanded configuration.

In the embodiment shown in FIG. 2, the fraction members 210 may extend radially outward from the snare member 200. The traction members 210 may be disposed on both the distal portion 202 and the proximal portion 204 of the snare member 200. However, in some embodiments, the traction members 210 may extend only along the distal portion 202. The traction members 210 may be designed such that traction (friction) between the snare member 200 and the target tissue may be enhanced. Increased traction between the fraction members 210 and the target tissue may facilitate improved gripping of the target tissue by the snare member 200. The traction members 210 may also facilitate improved gripping of the target tissue due to an increase in surface area of the snare member 200 in contact with the target tissue.

The traction members 210 may be discrete projections such as circular rings/discs disposed on the distal portion 202 of the snare member 200. Alternatively, traction members 210 may include any cross-sectional shape configured to engage tissue. For example, traction members 210 may include sharpened outer edges, or projections such as barbs, blades, conical protrusions, or teeth. In an embodiment, the traction members 210 may include rings and conical projections arranged in a pattern of alternating series over the distal portion 202. The shapes and configurations of the traction members 210 discussed herein are exemplary in nature, and it is understood that various other cross-sectional shapes such as rectangular, square, semicircular, ovular, hexagonal, pentagonal may also be employed.

In some embodiments, the traction members 210 may be formed from a separate element and disposed over the distal portion 202 of the snare member 200. The fraction members 210 may be temporarily or permanently coupled to the snare member 200 using any suitable technique such as but not limited to, welding, soldering, heat bonding, adhesive bonding, or the like. In addition, the traction members 210 may be comprised of tubular sections of material, such as nylon or polyolefin, that are configured to shrink or collapse when exposed to an energy source, such as heat or light, or chemical bath. The traction members 210 may also be applied by spraying or mask coating discrete sections of the distal portion 202 of the snare member 200 with a material to enhance traction, such as silicone or urethane. Alternatively, the traction members 210 may be integrally, e.g., monolithically formed with the snare member 200. Techniques such as but not limited to, grinding, etching, drawing, and so forth, may be used to form the traction members 210 integrally with the snare member 200.

In some embodiments, elements of the distal portion 202 of the snare member 200 may be coated, sprayed, or otherwise covered with a lubricious covering, such as polytetrafluoroethylene (PTFE), such that traction members 210 are the exposed (e.g. uncoated, masked, or uncovered) portions of the distal portion 202.

FIG. 3 illustrates an exemplary embodiment of a resection device 30 including one or more stress relief portions 312, according to an embodiment of the present disclosure. The resection device may include a snare member 300. The snare member 300 may include a distal portion 302 and a proximal portion 304. The distal portion 302 may have a smaller cross-sectional area than that of the proximal portion 304 as discussed above. Additionally, similarly to the embodiment of FIG. 1, snare member 300 may include transition portions 306 extending between the distal portion 302 and the proximal portion 304 of the snare member 200. In this embodiment, the transition portions 306 may include a gradual taper. Also, the snare member 300 may be coupled to push-pull member 308. The push-pull member 308 may extend and retract the snare member 300 and thereby transition the snare member 300 between the collapsed configuration and expanded configuration. Further, the snare member 300 may also include one or more traction members similar to the traction members 210 of FIG. 2.

As noted above, the snare member 300 may include one or more stress relief portions 312. In some embodiments, the stress relief portions 312 can be formed by removing small portions such as "corners" along an interior of the snare member 300 as shown in FIG. 3. Small portions of the snare member 300 may be removed by any appropriate means, such as, for example, cutting, etc. In operation, as the snare member 300 is tightened about target tissue by being pulled into a sheath or the like, it may transition from the expanded configuration into a partially collapsed configuration. That is, as the snare member 300 is pulled into the sheath, the snare member may transition from a fully expanded shape to a semi-expanded configuration in which the size of the snare member 300 extending distally of the sheath has been reduced. During such an operation, stress may be induced within the snare member 300. Such stress, however, may be directed towards the stress relief portions 312 and away from remaining portions, e.g., segments 314, of the snare member 300. As such, the loop of snare member 300 may maintain the desired shape, e.g., rectangular shape as shown in FIG. 3, longer while being retracted into the sheath. In other words, since the snare member 300 concentrates stress along stress relief portions 312 while allowing segments 314 to be relieved of stress build up, the snare member 300 is enabled to maintain its desired shape for a longer range of motion between the fully expanded configuration and the collapsed configuration within the sheath.

In some embodiments, the stress relief portions 312 may be disposed along the entire length of the snare member 300. In some embodiments, the snare member 300 may be shaped as a rectangular loop and include four stress relief portions 312 at the corners (e.g., points at which the snare loop changes directions) of the snare member 300 as shown in FIG. 3. In other embodiments, the snare member 300 may be hexagonal in shape and may include six stress relief portions 312. The number of stress relief portions 312 discussed herein are exemplary in nature, and for a person skilled in the art it is understood that various number of stress relief portions 312 such as, two, three, four, five, six, seven, eight, nine or the like may be contemplated.

FIG. 4 illustrates an exemplary embodiment of a resection device 40 having a variation in cross-sectional shape of a snare member 400, according to an embodiment of the present disclosure. The design and other considerations described for the snare member 100 may optionally also apply to the snare member 400. In one exemplary embodiment, the snare member 400 may include a distal portion 402 with a circular cross-sectional shape and a proximal portion 404 with a rectangular cross-sectional shape. As such, the distal portion 402 may exhibit increased flexibility relative to the proximal portion 404. Primarily, the increased flexibility of the distal portion 402 may allow for improved conformance of the snare member 400 to the tissue plane during a resection procedure. The improved conformance of the snare member 400 with the tissue plane may allow distal portion 402 of the snare member 400 to deform and stay in contact with a tissue plane so as to capture the target tissue. Further, one or more transition portions 406 may extend between the proximal portion 404 and the distal portion 402. In some embodiments, the proximal portion 404 and the distal portion 402 may be discrete elements coupled together at the transition portions 406. Exemplary techniques for coupling the distal portion 402 and the proximal portion 404 may include, soldering, welding, thermal boding, or pressure bonding.

The snare member 400 may include a continuous traction member 410 that may facilitate the snare member 400 in improved gripping of the tissue by increasing the traction between the snare member 400 and the target tissue. The traction member 410 may extend radially in all directions along the snare member 400. In some embodiments, the traction member 410 may be disposed over at least a portion of the distal portion 402. In some embodiments, a pair of the traction members 410 may be disposed bilaterally on the distal portion 402 or on either side of the snare member 400. In other embodiments, the traction member 410 may be present all along the snare member 400 i.e., on the proximal portion 404 as well as the distal portion 402.

FIG. 5 illustrates an enlarged view of a portion of the resection device 40 of FIG. 4. The snare member 400 is shown in a straight configuration, e.g., prior to being formed into a rounded loop of snare member 400. The distal portion 402 of the snare member 400 may have circular cross-sectional shape whereas the proximal portion 404 of the snare member 400 may have a rectangular cross-sectional shape. The transition portion 406 may be abrupt (e.g., sharp, nongradual) as it extends from the proximal portion 404 with rectangular cross-sectional shape to the distal portion 402 with circular cross-sectional shape. Alternatively, as described above, the transition portion 406 may comprise a gradual taper. The traction member 410 may extend distally from the transition portion 406 over at least a portion of the distal portion 402 in a helical, e.g., spiral arrangement so as to be continuous along its length. In some embodiments, the traction member 410 may be in the form of a double helical structure. In some embodiments, the traction member 410 may be arranged helically or spirally around a circumference of the snare member 400 along its complete length. The traction member 410 may be formed by any suitable technique such as, but not limited to, grinding, molding, machining, or etching. In some embodiments, the traction member 410 may be formed by disposing a sharp wire around the snare member 400. The traction member 410 may also be coupled to the snare member 400 by a suitable technique such as welding, soldering, and so forth. Accordingly, the traction member 410 may be either monolithically formed with the snare member 400 or discreetly formed and later coupled with snare member 400.

FIG. 6 illustrates an exemplary embodiment of a resection device 50 depicting an arrangement of fraction members 510 over a portion of a snare member 500, according to an embodiment of the present disclosure. As shown, the snare member 500 may include one or more traction members 510 of varying sizes extending radially outward. Any suitable arrangement of the discrete traction members 510 may be used. In some embodiments, the discrete traction members 510 may vary in shape selected from rectangular, square, semicircular, triangular, conical or the like. An alternating arrangement of the discrete traction members 510 with different shapes may also be contemplated. As shown in FIG. 5, the discrete traction members 510 extend along one side of the snare member 500. That is, upon being formed into a loop of the snare member 500, each of the fraction members 510 may extend towards a center of the loop of the snare member 500. Alternatively, however, traction members 510 may be disposed so as to extend from any side of the snare member 500. Accordingly, it is envisioned that the snare member 500 may have staggered discrete traction members 510.

FIGS. 7A and 7B illustrate an exemplary embodiment of a resection device during and upon completion of manufacturing, according to an embodiment of the present disclosure. As shown in FIG. 7A, the resection device 60 is in a straight configuration prior to formation into a loop. The resection device 60 may include a snare member 600 and a push-pull member 608 extending from the snare member. In some embodiments, the push-pull member 608 may act as a conducting means for electro-cauterization procedures, as described above. The snare member 600 may include one or more transitional portions 606 bridging a larger cross-sectional area proximal portion 604 with a smaller cross-sectional area distal portion 602. The snare member 600 may also include traction members 610 similar to the traction members 210, 410, and/or 510 discussed above. The snare member 600 may include two or more complementary mating members 614a and 614b. The complementary mating members 614a and 614b may be configured such that mating surfaces of each of the complementary mating members 614a and 614b are configured to couple to one another so as to form a loop, e.g., snare member 600. The complimentary mating members 614a and 614b may be configured to couple with one another through any appropriate engagement means, for example, a snap fit, a screw fit, a press fit, or the like. In some embodiments, the complementary mating members 614a may include protrusions and/or teeth and the complementary mating member 614b may include recess or holes to receive the protrusions or teeth thereby securing the two complementary mating members 614*a* and 614*b* together. As shown in FIGS. 7A and 7B, the complementary mating members 614*a* and 614*b* may have a larger cross-sectional area in comparison to a cross-sectional area of the snare member 600.

FIG. 8A illustrates an exemplary embodiment of coupler 820 for coupling a portion of a snare member in a closed loop configuration according to an embodiment of the present disclosure. The coupler 820 may be employed for attaching or coupling together the push-pull member 830 (shown in FIG. 8B) to secure the snare member. The coupler 820 may include a clip 840 such that the clip 840 includes one or more recesses 822 defined to receive the push-pull member 830. In some embodiments, the coupler 820 may be a sheath, band, housing or the like. The clip 840 may be dimensioned such that the clip 840 may couple with the push-pull member 830 by a suitable means including, but not limited to, a snap fit arrangement, an interference fit arrangement, and the like. The clip 840 may be disposed at different locations along the length of the push-pull member 830. In one embodiment, the clip 820 may be disposed proximate to the proximal portion (e.g., proximal portion 604 of FIGS. 7A-7B). However, in other embodiments, the clip 840 may be disposed at a proximal end of the push-pull member 830.

The push-pull member 830 may be formed with a reduced portion 832 as shown in FIG. 8B. The reduced portion 832 may have a reduced dimension (e.g., diameter) that may be inserted into the pair of recesses 822 of the clip 840. The reduced portion 832 may be formed using suitable techniques such as grinding, etching, machining or the like. In some embodiments, the push-pull member 830 may be formed using NITINOL wire. In some embodiments, the reduced portion 832 may be created by stretching. As such, the NITINOL wire may be stretched so as to form reduced portion 832, which is subsequently placed within the recesses 822 of the clip 840. Upon placement of the reduced portion 832 into clip 840, the push-pull member 830 may be allowed to substantially return to its original size thereby forming a press-fit engagement between clip 840 and reduced portion 832.

Another embodiment of forming a medical device (e.g., 10, 20, and 30) is disclosed. The method may include forming a loop of a snare member having a proximal portion and a distal portion. Once the loop of the snare member is formed, the snare member may be modified by varying the cross-sectional area of the distal portion so as to be different than a cross-sectional area of the proximal portion. In some cases, the cross-sectional area of the distal portion may be varied by removing a portion of material of the distal portion. The snare member may be modified to form a transition portion extending between the proximal portion and the distal portion. Some embodiments of the method may include forming one or more traction members that may extend along the snare member.

Characteristics of the embodiments include devices and methods with increased flexibility and control. Thus, the disclosed embodiments may provide the capability of resecting unwanted tissue with reduced risk of perforation of and/or damage to healthy surrounding tissue. The device with varied cross-sectional area may result in increased current density delivered to the unwanted target tissue during cutting, and thus, may allow for improved efficiency during cutting.

Other embodiments of the present disclosure will be apparent to those skilled in the art from consideration of the specification and practice of the embodiments disclosed herein. Combinations of the above embodiments, and other embodiments not specifically described herein, will be apparent to those of skill in the art upon reviewing the description. It is intended that the specification and examples be considered as exemplary only, with a true scope and spirit of the disclosure being indicated by the following claims.

What is claimed is:

1. A medical device, comprising:
a snare member consisting essentially of:
a first side portion having a first proximal portion and a first distal portion, wherein the first proximal portion has a larger cross-section than the first distal portion;
a second side portion having a second proximal portion and a second distal portion, wherein the second proximal portion has a larger cross-section than the second distal portion;
a distal connecting portion connecting the first distal portion and the second distal portion; and
a first mating member connected to the first proximal portion and a second mating member connected to the second proximal portion, wherein the first mating member is operative to couple to the second mating member, and wherein the first proximal portion, the first distal portion, the distal connecting portion, and the first and the second mating members are formed of a continuous piece of material; and
an operating member extending proximally of the snare member and configured to extend and retract the snare member.

2. The medical device of claim 1, wherein the first side portion includes:
a plurality of traction members formed of the continuous piece of material, wherein each of the plurality of traction members is spaced from an adjacent traction member of the plurality of traction members and is configured to extend radially outwardly from the first side portion.

3. The medical device of claim 2, wherein the plurality of traction members is a first plurality of traction members,
wherein the second side portion includes a second plurality of traction members formed of the continuous piece of material, wherein each of the second plurality of traction members is spaced from an adjacent traction member of the second plurality of traction members and is configured to extend radially outwardly from the second side portion, and
wherein each of the traction members of the first and second plurality of traction members has a cross-sectional shape selected from the following: rectangular, square, semi-circular, ovular, and polygonal.

4. The medical device of claim 3, wherein each of the first plurality of traction members extends in a first same direction outward from the first side portion; and wherein each of the second plurality of traction members extends in a second same direction outward from the second side portion.

5. The medical device of claim 4, wherein each of the first plurality of traction members extends orthogonally from the first side portion, and wherein each of the second plurality of traction members extends orthogonally from the second side portion.

6. The medical device of claim 5, wherein the first and the second mating members each has a larger cross-section than the first proximal portion or the second proximal portion.

7. The medical device of claim 6, wherein the first mating member includes a recess and the second mating member includes a protrusion.

8. The medical device of claim 7, wherein the first mating member includes a plurality of recesses, and the second mating member includes a plurality of protrusions.

9. The medical device of claim 5, wherein the first plurality of traction members extends from the first side portion approximately midway between the first mating member and the distal connecting portion, and wherein the second plurality of traction members extends from the second side portion approximately midway between the first mating member and the distal connecting portion.

10. The medical device of claim 3, wherein at least one traction member of the first or second plurality of traction members has a different cross-sectional shape than at least one other traction member of the first or second plurality of traction members.

11. The medical device of claim 1, wherein the first side portion includes:
at least one traction member extending along the first side portion, wherein the at least one traction member is a continuous spiral coiled around the first side portion.

12. The medical device of claim 11, wherein the at least one traction member is a first traction member, and
wherein the second side portion includes a second traction member extending along the second side portion, wherein the second traction member is a continuous spiral coiled around the second side portion.

13. The medical device of claim 1, wherein the cross-sectional shape of each of the first and second distal portions is circular and the cross-sectional shape of each of the first and second proximal portions is non-circular.

14. A medical device, comprising:
a snare member consisting essentially of:
a first side portion having a first proximal portion and a first distal portion, wherein the first distal portion is more flexible than the first proximal portion;
a second side portion having a second proximal portion and a second distal portion, wherein the second distal portion is more flexible than the second proximal portion;
a distal connecting portion connecting the first distal portion and the second distal portion; and
a first mating member connected to the first proximal portion and a second mating member connected to the second proximal portion, wherein the first mating member is operative to couple to the second mating member, and wherein the first proximal portion, the first distal portion, the distal connecting portion, and the first and the second mating members are formed of a continuous piece of material; and
an operating member extending proximally of the snare member and configured to extend and retract the snare member.

15. The medical device of claim 14, wherein a cross-sectional area of each of the first and second distal portions is smaller than a cross-sectional area of each of the respective first and second proximal portions, and wherein a cross-sectional shape of each of the first and second distal portions is circular and a cross-sectional shape of each of the first and second proximal portions is non-circular.

16. The medical device of claim 15, wherein the first side portion includes:
a plurality of traction members formed of the continuous piece of material, wherein each of the plurality of traction members is spaced from an adjacent traction member of the plurality of traction members and is configured to extend radially outwardly from the first side portion.

17. The medical device of claim 16, wherein the plurality of traction members is a first plurality of traction members,
wherein the second side portion includes a second plurality of traction members formed of the continuous piece of material, wherein each of the second plurality of traction members is spaced from an adjacent traction member of the second plurality of traction members and is configured to extend radially outwardly from the second side portion, and
wherein each of the traction members of the first and second plurality of traction members has a cross-sectional shape selected from the following: rectangular, square, semi-circular, ovular, and polygonal.

18. The medical device of claim 16, wherein at least one traction member of the first or second plurality of traction members has a different cross-sectional shape than at least one other traction member of the first or second plurality of traction members.

19. The medical device of claim 15, wherein the first side portion includes:
at least one traction member extending along the first side portion, wherein the at least one traction member is a continuous spiral coiled around the first side portion.

20. The medical device of claim 19, wherein the at least one traction member is a first traction member, and
wherein the second side portion includes a second traction member extending along the second side portion of the snare member opposite the first side portion, wherein the second traction member is a continuous spiral coiled around the second side portion.

\* \* \* \* \*